United States Patent [19]

Stoddart et al.

[11] Patent Number: 4,817,623
[45] Date of Patent: Apr. 4, 1989

[54] METHOD AND APPARATUS FOR INTERPRETING OPTICAL RESPONSE DATA

[75] Inventors: Hugh F. Stoddart, Groton, Mass.; Gary D. Lewis, St. Clair Shores, Mich.

[73] Assignee: Somanetics Corporation, Troy, Mich.

[21] Appl. No.: 830,578

[22] Filed: Feb. 18, 1986

Related U.S. Application Data

[63] Continuation-in-part of Ser. No. 542,022, Oct. 14, 1983, Pat. No. 4,570,638.

[51] Int. Cl.$^4$ .............................................. A61B 6/08
[52] U.S. Cl. .................................................... 128/665
[58] Field of Search ...................... 128/633, 665, 664; 356/432

[56] References Cited

U.S. PATENT DOCUMENTS

| | | | |
|---|---|---|---|
| 738,707 | 9/1903 | VanNort | 362/280 |
| 2,358,992 | 9/1944 | Millikan | 356/41 |
| 2,414,747 | 1/1947 | Kirschbaum | 128/204.23 |
| 2,423,855 | 7/1947 | Smaller | 356/41 |
| 2,437,916 | 3/1948 | Greenwald | 128/665 |
| 2,439,857 | 4/1948 | Millikan | 356/41 |
| 2,442,462 | 6/1948 | Kirschbaum | 128/633 |
| 2,475,132 | 7/1949 | Ergen | 618/378 |
| 2,640,389 | 6/1953 | Liston | 128/633 |
| 2,685,815 | 8/1954 | Mayne | 128/633 |
| 2,706,927 | 4/1955 | Wood | 356/41 |
| 2,760,485 | 8/1956 | Adelman | 128/633 |
| 2,790,438 | 4/1957 | Taplin et al. | 128/633 |
| 3,036,568 | 5/1962 | Stark | 128/664 |
| 3,123,066 | 3/1964 | Brumley | 128/634 |
| 3,136,310 | 6/1964 | Meltzer | 128/634 |
| 3,152,587 | 10/1964 | Ullrich et al. | 128/633 |
| 3,280,636 | 10/1966 | Tomberg | 73/432 |
| 3,313,290 | 4/1967 | Chance et al. | 128/633 |
| 3,335,716 | 8/1967 | Alt et al. | 128/664 |
| 3,349,762 | 10/1967 | Kapany | 128/666 |
| 3,406,681 | 10/1968 | Zandman | 128/645 |
| 3,412,729 | 11/1968 | Smith, Jr. | 128/633 |
| 3,461,856 | 8/1969 | Polanyi | 128/633 |
| 3,511,227 | 5/1970 | Johnson | 128/666 |
| 3,517,999 | 6/1970 | Weaver | 356/32 |
| 3,527,932 | 9/1970 | Thomas | 128/23 |
| 3,602,213 | 8/1971 | Howell et al. | 128/2.05 P |
| 3,628,525 | 12/1971 | Polanyl et al. | 128/2.05 P |
| 3,672,352 | 6/1972 | Summers | 128/2 R |
| 3,674,013 | 7/1972 | Polanyl | 128/2.05 D |
| 3,677,648 | 7/1972 | Dorsch | 356/40 |
| 3,690,769 | 9/1972 | Mori | 356/41 |
| 3,704,706 | 12/1972 | Herczfeld et al. | 128/2 R |
| 3,710,011 | 1/1973 | Altemus et al. | 128/5.4 R |
| 3,734,091 | 5/1973 | Taplin | 128/142 |
| 3,748,471 | 7/1973 | Ross et al. | 250/333 |
| 3,769,963 | 11/1973 | Goldman et al. | 128/2 R |

(List continued on next page.)

FOREIGN PATENT DOCUMENTS

| | | | |
|---|---|---|---|
| 484366 | 6/1977 | Australia | 128/633 |
| 3015 | 7/1979 | European Pat. Off. | 356/41 |

(List continued on next page.)

OTHER PUBLICATIONS

"Medical & Biological Engineering & Computing", vol. 17, No. 3, May, 1979, p. 419, Physiological Light-Emitting Diode Photocell Monitor.

(List continued on next page.)

Primary Examiner—Francis J. Jaworski
Attorney, Agent, or Firm—Price, Heneveld, Cooper, DeWitt & Litton

[57] ABSTRACT

The internal physiological compositional state of an individual examination subject for example a human breast is assessed by transmission of selected light energy spectra into the interior of such subject, detecting the selected spectra after transversal of a distance within the object, quantifying the detected light energy at selected wavelengths, conditioning the obtained value sequence on the basis of distance, determining at least one composite averaged value from the conditioned value, and using such as a characterizing value in comparison with analogously obtained values representative for example of a norm in order to asses the internal state of the subject.

25 Claims, 6 Drawing Sheets

U.S. PATENT DOCUMENTS

| | | | |
|---|---|---|---|
| 3,769,974 | 11/1973 | Smart et al. | 128/633 |
| 3,777,738 | 12/1973 | Sugita et al. | 128/2 T |
| 3,787,119 | 1/1974 | Rybak | 356/73 |
| 3,814,081 | 6/1974 | Mori | 128/2 L |
| 3,822,695 | 7/1974 | Takayama | 128/2 L |
| 3,847,483 | 11/1974 | Shaw et al. | 356/41 |
| 3,881,481 | 5/1975 | Huele et al. | 128/2.05 V |
| 3,889,656 | 6/1975 | Krawitt | 128/2 R |
| 3,910,701 | 10/1975 | Henderson et al. | 128/625 |
| 3,958,560 | 5/1976 | March | 128/2.05 E |
| 3,963,019 | 6/1976 | Quandt | 128/2 T |
| 3,980,075 | 9/1976 | Heule | 128/205 T |
| 3,987,303 | 10/1976 | Stoft et al. | 250/343 |
| 3,993,047 | 11/1976 | Peek | 128/2.05 P |
| 4,013,067 | 3/1977 | Kresse et al. | 128/2.05 R |
| 4,014,321 | 3/1977 | March | 128/2 A |
| 4,015,595 | 4/1977 | Benjamin, Jr. | 128/2.05 V |
| 4,029,085 | 6/1977 | DeWitt et al. | 128/2 R |
| 4,030,485 | 6/1977 | Warner | 128/2 R |
| 4,041,933 | 8/1977 | Reichenberger | 128/2 E |
| 4,048,493 | 9/1977 | Lee | 250/205 |
| 4,063,551 | 12/1977 | Sweeney | 128/2.05 P |
| 4,073,292 | 2/1978 | Edelman | 128/214 E |
| 4,086,616 | 4/1978 | Catano et al. | 358/81 |
| 4,109,643 | 8/1978 | Bond et al. | 128/2 L |
| 4,109,647 | 8/1978 | Stern et al. | 128/2.05 F |
| 4,114,604 | 9/1978 | Shaw et al. | 128/2 L |
| 4,123,172 | 10/1978 | French | 356/188 |
| 4,157,708 | 6/1979 | Imura | 128/666 |
| 4,163,447 | 8/1979 | Orr | 128/666 |
| 4,166,695 | 9/1979 | Hill et al. | 356/28 |
| 4,167,331 | 9/1979 | Nielsen | 356/39 |
| 4,170,987 | 10/1979 | Anselmo et al. | 128/665 |
| 4,175,545 | 11/1979 | Termanini | 128/666 |
| 4,178,917 | 12/1979 | Shapiro | 128/665 |
| 4,183,360 | 1/1980 | Carlson et al. | 128/666 |
| 4,198,988 | 4/1980 | Cash, Jr. et al. | 128/666 |
| 4,202,339 | 5/1980 | Wirtzfeld et al. | 128/419 PG |
| 4,207,892 | 6/1980 | Binder | 128/665 |
| 4,212,306 | 7/1980 | Mahmud | 128/665 |
| 4,213,462 | 7/1980 | Sato | 128/634 |
| 4,222,389 | 9/1980 | Rubens | 128/633 |
| 4,223,680 | 3/1979 | Jobsis | 128/633 |
| 4,236,526 | 12/1980 | Richard | 128/633 |
| 4,241,738 | 12/1980 | Lubbers et al. | 128/666 |
| 4,249,540 | 2/1981 | Koyama et al. | 128/666 |
| 4,253,447 | 3/1981 | Moore et al. | 128/6 |

(List continued on next page.)

FOREIGN PATENT DOCUMENTS

| | | | |
|---|---|---|---|
| 19478 | 11/1980 | European Pat. Off. | 318/678 |
| 23186 | 1/1981 | European Pat. Off. | 356/41 |
| 46601 | 3/1982 | European Pat. Off. | 128/645 |
| 2023318 | 12/1971 | Fed. Rep. of Germany | 128/633 |
| 2053301 | 5/1972 | Fed. Rep. of Germany | 128/633 |
| 2263890 | 7/1973 | Fed. Rep. of Germany | 128/2.05 D |
| 2065515 | 3/1974 | Fed. Rep. of Germany | 128/2 R |
| 2430788 | 10/1975 | Fed. Rep. of Germany | 128/23 |
| 2538985 | 5/1976 | Fed. Rep. of Germany | 356/41 |
| 2517129 | 6/1976 | Fed. Rep. of Germany | 356/32 |
| 2641144 | 3/1977 | Fed. Rep. of Germany | 356/41 |
| 2741913 | 4/1978 | Fed. Rep. of Germany | 128/2 T |
| 2741981 | 4/1978 | Fed. Rep. of Germany | 250/333 |
| 2724543 | 12/1978 | Fed. Rep. of Germany | 128/2.05 V |
| 2726606 | 12/1978 | Fed. Rep. of Germany | 128/2 L |
| 2827488 | 2/1979 | Fed. Rep. of Germany | 128/2 T |
| 2823769 | 12/1979 | Fed. Rep. of Germany | 250/343 |
| 2947194 | 7/1981 | Fed. Rep. of Germany | 128/2 R |
| 2481917 | 11/1981 | France | 128/666 |
| 2517953 | 6/1983 | France | 128/634 |
| 149157 | 7/1981 | German Democratic Rep. | 128/633 |
| 54-129786 | 10/1979 | Japan | 128/2 R |
| 124701 | 12/1959 | U.S.S.R. | 128/666 |
| 146905 | 6/1962 | U.S.S.R. | 128/666 |
| 283670 | 1/1971 | U.S.S.R. | 128/634 |
| 311618 | 5/1972 | U.S.S.R. | 128/665 |
| 680725 | 8/1979 | U.S.S.R. | 128/666 |
| 696378 | 11/1979 | U.S.S.R. | 128/666 |
| 704598 | 12/1979 | U.S.S.R. | 128/635 |
| 786983 | 12/1980 | U.S.S.R. | 128/633 |
| 824995 | 4/1981 | U.S.S.R. | 128/633 |
| 745646 | 2/1956 | United Kingdom | 128/2 A |
| 777651 | 6/1957 | United Kingdom | 356/188 |
| 2068537A | 8/1981 | United Kingdom | 128/665 |
| 2076963A | 12/1981 | United Kingdom | 128/2 L |
| 2092856A | 8/1982 | United Kingdom | 128/366 |

OTHER PUBLICATIONS

"Medical & Biological Engineering & Computing", vol. 20, No. 1, Jan., 1982, p. 111, Development of an Optical Fibre Technique For He-Ne Laser Screening of Human Body and Its Comparison with the Integrating Sphere Method.

(List continued on next page.)

U.S. PATENT DOCUMENTS

| | | | |
|---|---|---|---|
| 4,253,744 | 3/1981 | Sawa | 351/16 |
| 4,259,948 | 4/1981 | Urban | 128/6 |
| 4,259,963 | 4/1981 | Huch | 128/635 |
| 4,261,344 | 4/1981 | Moore et al. | 128/6 |
| 4,266,554 | 5/1981 | Hamaguri | 128/633 |
| 4,267,844 | 5/1981 | Yamanishi | 128/633 |
| 4,281,645 | 8/1981 | Jobsis | 128/633 |
| 4,286,602 | 9/1981 | Guy | 128/665 |
| 4,290,433 | 9/1981 | Alfano | 128/665 |
| 4,295,470 | 10/1981 | Shaw et al. | 128/634 |
| 4,305,398 | 12/1981 | Sawa | 128/633 |
| 4,312,357 | 1/1982 | Andersson et al. | 128/664 |
| 4,321,930 | 3/1982 | Jobsis | 128/633 |
| 4,331,132 | 5/1982 | Mukasa | 128/6 |
| 4,332,258 | 6/1982 | Arai et al. | 128/666 |
| 4,336,809 | 6/1982 | Clark | 128/665 |
| 4,339,954 | 7/1982 | Anson et al. | 73/657 |
| 4,344,438 | 8/1982 | Schultz | 128/634 |
| 4,350,163 | 9/1982 | Ford, Jr. et al. | 128/633 |
| 4,365,307 | 12/1982 | Tatsuwaki et al. | 364/557 |
| 4,366,381 | 12/1982 | Fischer et al. | 250/316.1 |
| 4,370,986 | 2/1983 | Gebhart et al. | 128/716 |
| 4,380,240 | 4/1983 | Jobsis et al. | 128/633 |
| 4,423,736 | 1/1984 | DeWitt et al. | 128/633 |
| 4,446,871 | 1/1980 | Imura | 128/633 |
| 4,467,812 | 8/1984 | Stoller | 128/665 |
| 4,495,949 | 1/1985 | Stoller | 128/664 |
| 4,510,938 | 4/1985 | Jobsis et al. | 128/633 |
| 4,515,165 | 5/1985 | Carroll | 128/665 |
| 4,541,438 | 9/1985 | Parker et al. | 128/664 |
| 4,570,638 | 2/1986 | Stoddart et al. | 356/432 |
| 4,592,361 | 6/1986 | Parker et al. | 128/633 |
| 4,600,011 | 7/1986 | Watmough | 128/664 |
| 4,616,657 | 10/1986 | Stoller | 128/664 |
| 4,649,275 | 3/1987 | Nelson et al. | 128/664 |
| 4,651,743 | 3/1987 | Stoller | 128/664 |
| 4,655,225 | 4/1987 | Dähne et al. | 128/664 |

OTHER PUBLICATIONS

"Analytical Chemistry", vol. 52, No. 6, May, 1980, p. 864, Fiber Optic pH Probe for Physiological Use.

"Medical Instrumentation", vol. 9, No. 3 (May-Jun., 1975), p. 136 Continuous *In Vivo* Assessment of Arteriovenous Oxygen Difference Utilizing a Fiberoptic Catheter Oximeter.

"Biomedical Engineering & Computing", vol. 5, No. 11 (U.K.), Nov. 1970, p. 54 A New Instrument for Rapid Measurement of Blood Oxygen Saturation and Hb Concentration.

"Medical Instrumentation", vol. 13, No. 4 (Jul.-Aug., 1979), p. 232, A Versatile Simultaneous Multifinger Photocell Plethysmography System for Use in Clinical and Occupational Medicine.

"IEEE Transactions on Biomedical Engineering", vol. BME-22 No. 3, May, 1975, p. 183 & Title cover, The Choroidal Eye Oximeter: An instrument for Measuring Oxygen Saturation of Choroidal Blood *In Vivo*.

"IEEE Transactions on Biomedical Engineering" vol. BME-26 No. 4, Apr., 1979, p. 220, Applications of Photoacoustic Spectroscopy to Problems in Dermatology Research.

The Waters Company Advertisement, received in PTO 10/7/65 on X-350 Oximeter (Rochester, Minn.).

IBM Technical Disclosure Bulletin, vol. 10 No. 3, Aug., 1967 "Stacker Selection System" by A. K. Brooks & C. J. Kellerman, pp. 225-226.

IBM Technical Disclosure Bulletin, vol. 10, No. 3, Aug., 1967 "MICR Automatic Gain Control" by R. W. Arnold, pp. 227-228.

"Biomedizinische Technik" (Germany) Band 17 1972 No. 3, p. 93.

"Biomedizinische Technik" (Germany) Band 18 1973 No. 4, p. 142.

"Medical & Biological Engineering & Computing", Jan., 1980, p. 27 Spectrophotometric monitoring of arterial oxygen saturation in the fingert.

"Medical and Biological Engineering & Computing", Nov., 1979, p. 763, Backscattering of Light by Red Cell Suspensions.

"Medical & Biological Engineering & Computing", Mar., 1980, p. 250, Picosecond Laser Stereometry Light Scattering Measurements on Biological Material.

"IEEE Transactions on Biomedical Engineering" vol. BME-26, No. 7 Jul., 1979, p. 416, A Neonatal Fiberoptic Probe for Oximetry and Dye Curves.

"IEEE Transactions on Biomedical Engineering" vol. BME-23, No. 5, Sept., 1976, p. 391 & Title cover, Multiple Scattering Analysis of Retinal Blood Oximetry.

"IEEE Transactions on Biomedical Engineering" vol. BME-25, No. 1 Jan., 1978, p. 28, An Instrument to Measure Cutaneous Blood Flow Using the Doppler Shift of Laser Light.

(List continued on next page.)

OTHER PUBLICATIONS

"Biomedical Engineering" (U.S.A.), vol. 12, No. 1, Jan.-Feb., 1978, (published 9/78), p. 20, Instrument for Measuring Microconcentrations of Indicator Dyes in Blood.

"Chest, 76", Jul. 1, 1979, p. 27 Fluorescence Bronchoscopy for Detection of Lung Cancer.

"Review of Scientific Instruments", vol. 51, No. 10, Oct., 1980, p. 1403, Endoscopic System for Simultaneous Visual Examination and Electronic Detection of Fluorescence.

"1979" IEEE International Solid State Circuits Conference, Pennsylvania, Feb., 14–16, 1979, p. 202, Session XV: Solid-State Imaging and Biomedical Applications.

"Journal of Biomedical Engineering", vol.4, No. 2, Apr., 1982, p. 142 An Infra-Red Reflectance System for Ambulatory Characterization of Left Ventricular Function.

"IEEE 1979 Frontiers of Engineering in Health Care Conference", Denver, Colo., U.S.A., p. 209, Session 9: Pulse Rate Monitor.

"Medical & Biological Engineering", vol. 6, 1968 (U.K.), p. 409, Tissue Identification During Needle Puncture by Reflection Spectrophotometry.

"Medical & Biological Engineering", vol. 10, 1972 (U.K.), p. 385, A Light Emitting Diode Skin Reflectance Oximeter.

"Medical & Biological Engineering & Computing", vol. 18, No. 3, May, 1980, p. 265, Self-stabilising System for Measuring Infrared Light Back-scattered from Vaginal Tissue.

"The American Journal of Cardiology", vol. 49, Mar., 1982, p. 743, Simultaneous Measurement of Coronary Venous Blood Flow and Oxygen Saturation During Transient Alterations in Myocardial Oxygen Supply and Demand.

"SPIE", (Soc. Photo-Optical Instrumentation Engineering), vol. 211, (1979), p. 128, Subpicosecond Spectroscopic Techniques in Biological Materials.

"EDN", Sep. 20, 1980, vol. 25, No. 17, p. 69, Fitness and Health-Care Products Incorporate Advanced Electronics.

"Hewlett-Packard Journal", vol. 28, No. 2, Oct. 1976, p. 2 & Title Cover Sheet, Continuous, Non-Invasive Measurements of Arterial Blood Oxygen Levels.

"Laser Electro Optic", No. 1, (1978), U.S.A., p. 22, A Non-Contact High Sensitivity Laser Stethoscope.

"Medicamundi", vol. 17, No. 1, (1972), Abstract & pg. 7, The Principle, Design and Features of a New Hb-Oximeter.

"Vestnik Dermatologi i Venerologii", (Russian), vol. 35, Jun., 1961, pp. 17–20 & 1st sheet of translation, The Role of the Luminescence Method in the Diagnosis of Some Dermatoses.

"Proceedings of the 26th Annual Conference on Engineering in Medicine & Biology", Minneapolis, Minn. Sep. 30–Oct. 4, 1973, p. 276, Improved Extracorporeal Reflectance Oximeter.

"Proceedings of the Thirteenth ISA Aerospace Instrumentation, Symposium", San Diego, Calif. Jun. 13–Jun. 16, 1967, p. 489 & Title Cover, New Horizons in Biomedical Instrumentation.

"IRE" Transactions on Medical Electronics, Jul. 1958, Contents page and Copyright Notice, note p. 34, article on Oximetry by W. Paul.

"IEEE Transactions on Biomedical Engineering", vol. BME-24, No. 2, Mar. 1977, A Proposed Miniature Red/Infrared Oximeter Suitable for Mounting on a Catheter Tip.

"Medical Instrumentation", vol. 7, No. 4, Sep.-Oct. 1973, p. 262, Oxygen Saturation Monitor for Extra-Corporeal Circulation Applications.

"IEEE Transactions on Biomedical Engineering", vol. BME-25, No. 1, Jan. 1978, p. 94, An Electronic Circuit for Red/Infrared Oximeters.

"American Journal of Clinical Nutrition 40", Dec. 1984, pp. 1123–1130, A New Approach for the Estimation of Body Composition: Infrared Interactance.

"Journal of Food Science", vol. 48, 1983, pp. 471–474, Determination of Moisture, Protein, Fat and Calories in Raw Pork, Beef by Near Infrared Spectroscopy.

"Journal of Food Science", vol. 49, 1984, pp. 995–998, Application for Near Infrared Spectroscopy for Predicting the Sugar Content of Fruit Juices.

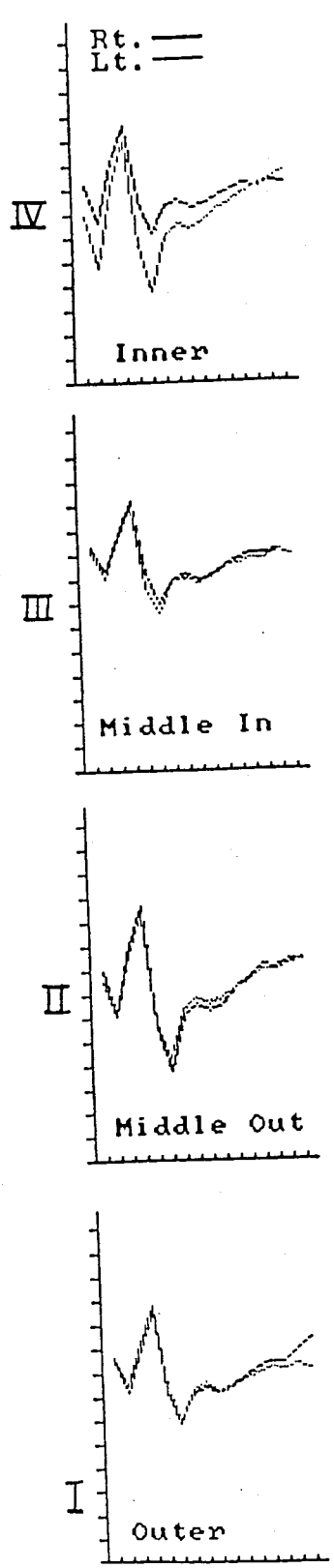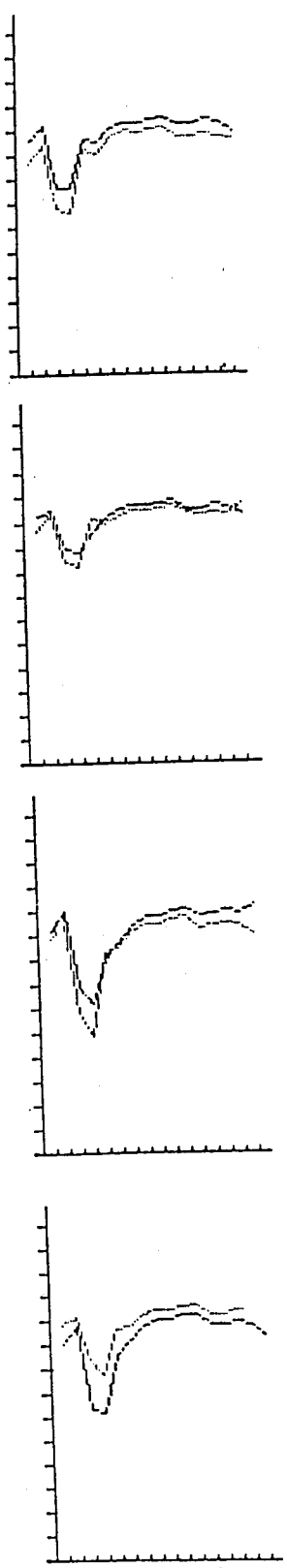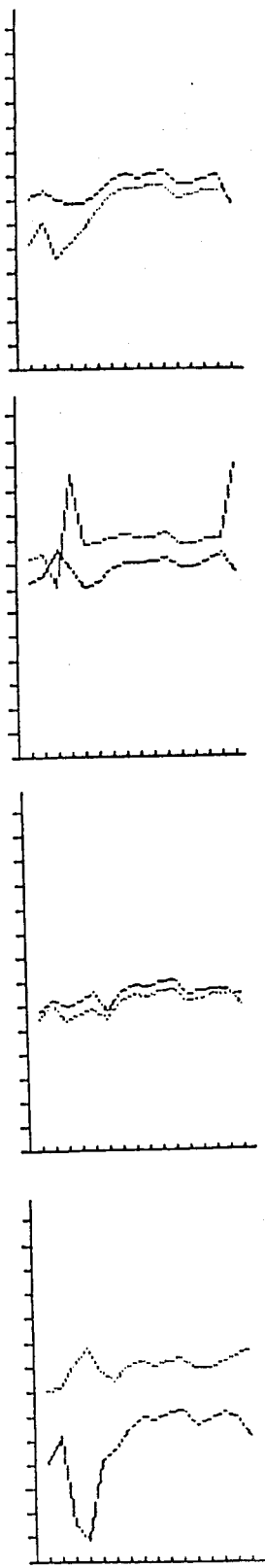
Fig. 3a.  Fig. 3b.  Fig. 3c.
Fig. 3.

METHOD AND APPARATUS FOR INTERPRETING OPTICAL RESPONSE DATA

CROSS-REFERENCE TO RELATED APPLICATIONS

This application is a continuation-in-part of Applicants' co-pending application Ser. No. 542,022, filed Oct. 14, 1983, now U.S. Pat. No. 4,570,638, and is related to Applicants' co-pending application Ser. Nos. 827,526 and 830,567, which are incorporated herein by reference.

TECHNICAL FIELD

This invention relates generally to optical response apparatus and methodology, i.e., the utilization of light energy as an investigative media in consideration and/or evaluation of internal tissue condition or state, accomplished by the infusion of specially-selected and/or specially-applied light energy into the tissue to be evaluated or analyzed and the resultant determination of the particular optical response of the subject to such light energy. Somewhat more particularly, the invention relates to diagnostic or clinical investigative apparatus and methodology which utilizes selected light spectra to assess the physiological state or condition of biological material, e.g., tissue, bone, etc., particularly on an in vivo and in situ basis, from the standpoint of transmissivity, or transmissibility, of the subject to the selected light spectra which are applied. Particular examples of apparatus and methodology exemplifying such investigative procedures are those disclosed in Applicants' above-referenced copending applications for U.S. Patent, including Ser. No. 542,022 (now U.S. Pat. No. 4,570,638) and Ser. No. 827,526, filed Feb. 10, 1986, both of which are incorporated herein by reference.

More particularly still, the present invention relates to the novel treatment (processing), interpretation, and presentation of optical response data obtained from examination of matter, particularly biological material, and especially including living tissue, in particular live human anatomical tissue, for example the internal tissue of the human breast.

BACKGROUND OF THE INVENTION

In Applicants' above-referenced and incorporated co-pending applications for U.S. Patent, novel apparatus and methodology are disclosed for examining, and appraising the physiologic or compositional state or condition of, biological (organic) material; in particular, for conducting in vivo examination and assessment of the physiological state or condition of human tissue, for example diagnostic examination of the breast (or other anatomical portion) of live human subjects.

In accordance with the above-noted referenced and incorporated methodology and apparatus, selected light spectra are introduced into the subject being examined at selected locations, and the light energy so infused is then received (e.g., detected) at other particular locations, preferably including a pair of such other locations, for example, a "near" location closer to the point of light infusion and a "far" location disposed more remote from that point. As described more fully in the referenced co-pending applications, the use of at least two such receivers and the distances between the point of initial light insertion and the points of light reception are important factors in the useful application of the resulting data (i.e., the measured values of light intensity as determined by the detectors themselves).

Thus, the "optical probe" by which the optical response data is obtained incorporates means whereby the particular distance between the two optical "heads" (i.e., the light-producing and the light-receiving instrumentalities) may be determined in any given position to which the two such heads are adjusted to accommodate the size of a particular subject of examination. Such distance determinations, which may be designated "nominal optical distances", are inputs into the computing apparatus which is used to process the data, where they are utilized with other computation processes to "condition" or convert the "raw" data from the detectors so that it becomes representative of the intrinsic internal tissue composition of the subject under examination, i.e., independent of factors such as specimen (e.g., breast) thickness and boundary effects (e.g., skin pigmentation, etc.).

Such "conditioned" data, representative of intrinsic internal physiological state or condition, is of great value in portraying and understanding the actual internal nature of the particular tissue under examination, and a particularly useful manner in which such tissue characterization may be presented and apprehended is, as disclosed in co-pending application Ser. No. 542,022 (now U.S. Pat. No. 4,570,638) by way of graphical presentations which constitute, in effect, spectrally-based, optical "profiles" of a given patient or other subject. As noted in this patent, such points may be visually contrasted in different ways with other such profiles, whether representative of the same patient or subject or other patients or subjects. For example, in human breast examination, comparison may be made to other profiles taken at adjacent or related positions on the same breast, and in contralateral studies, where profiles taken at the same locations on opposite breasts of the same patient are compared to one another. Additionally, such "profiles" may very advantageously be compared with other analogous profiles taken from other patients, whereby variations and abnormalities may be noted and taken under consideration.

Additionally, as disclosed and discussed in co-pending and related application Serial No. 830,567, the "conditioned" optical response data from which the aforementioned profiles are prepared may very advantageously be further conditioned by compiling broadly-based averages of such data obtained from large numbers of previously-examined subjects and subtracting such average values from the conditioned data for new subjects under current examination, whereby the conditioned new examination data is in effect recast into a form which more vividly portrays anomalies and departures from the norm. Such recast data may then be graphically presented as modified patient (or subject) profiles which, in addition to interpretation on the basis of shape, contour, etc., and by comparison to other such profiles (e.g., in contralateral studies of the same patient, or by comparison to profiles representative of "normal" or typical such subjects), the new (modified) profiles are also found to be directly indicative of relative internal substance, content, and composition, by which a far greater understanding of the subject matter may be obtained, as well as a more comprehensive diagnostic judgment.

SUMMARY OF THE INVENTION

The present invention carries forward the teachings and methodology presented in the above-referenced, incorporated, prior and co-pending applications, in particular that which is the subject of Applicants' prior and co-pending application Ser. No. 542,022, now U.S. Pat. No. 4,570,638 and application Ser. No. 830,567. More particularly, the present invention discloses further attributes and novel utilization of the aforementioned "conditioned" light energy intensity data received at the aforesaid pair of locations ("near" and "far", or otherwise selectively located) on the subject being examined, in accordance with which the conditional state of the subject under study may be apprehended, and analytically defined. Thus, the invention contemplates a more extensive as well as deeper comprehension of the optical response examination data as well as certain novel screening and detection procedures and, accordingly, contemplates the possibility of increased early warning of the advent of abnormal changes which may signify the presence or onset of disease, degradation, or other undesirable internal tissue condition.

Still more particularly, the present invention contemplates, and provides, for the further "conditioning" of the spectrally-based optical response data referred to above, together with the preparation and utilization of further graphic presentations of patient or subject "profiles" based upon such further conditioned optical data. In accordance with such procedures, interpretative conclusions may be formed and distinctions made with respect to defined population bases, leading to and helping to establish criteria and methodology by which automated machine, interpretation of data is made possible. Such automated interpretation is in fact instituted in accordance with the invention, providing for substantially instantaneous analysis, interpretation, and classification of the conditioned optical response data, avoiding all subjective or personal bias or influence and enabling extremely consistent and accurate analytical results. Preferably, such automated, machine analysis of conditioned optical response data occurs in the form of classification designation, i.e., selection of one particular classification or category from a number of possible alternatives whose characterizing parameters are previously established, the entire series of such classifications or categories together characterizing the complete range of possible results, for example on the basis of risk or anomaly percentage.

Accordingly, the present invention provides methodology and apparatus in accordance with which the existing physiological or conditional state of a patient or other subject may be appraised on an ongoing metabolic basis, without use of any invasive agency or any ionized radiation, with the tissue or other substance being observed on an in vivo and in situ basis without disruption or modification of natural processes or state. The resulting information may be taken periodically from the same patient, and observed on a time-comparative basis, and/or it may be compared to normative values, prepared from large populations, for rapid, accurate and consistent programmed diagnostic evaluation or analysis of the state of the patient or subject under consideration, in a manner unlike any other known instrumentality presently in comparable use.

The advantages provided and objectives satisfied by the aforementioned improvements will become more apparent and better understood by reference to the ensuing specification, which describes certain preferred embodiments to illustrate the underlying concept, together with reference to the appended drawings depicting the particularities of such preferred embodiments.

BRIEF DESCRIPTION OF THE DRAWINGS

In the drawings:

FIGS. 3a, 3b, and 3c are composite graphical presentations of optical response profiles taken from Applicants' co-pending application Ser. No. 542,022, now U.S. Pat. No. 4,570,638;

DETAILED DESCRIPTION OF PREFERRED EMBODIMENTS

Figure 2:
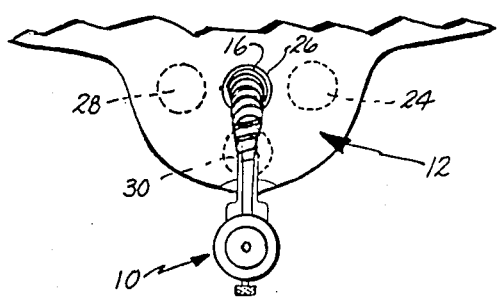
FIG. 2 is a fragmentary, pictorial overhead plan view of the subject matter shown in FIG. 1.
Figure 1:
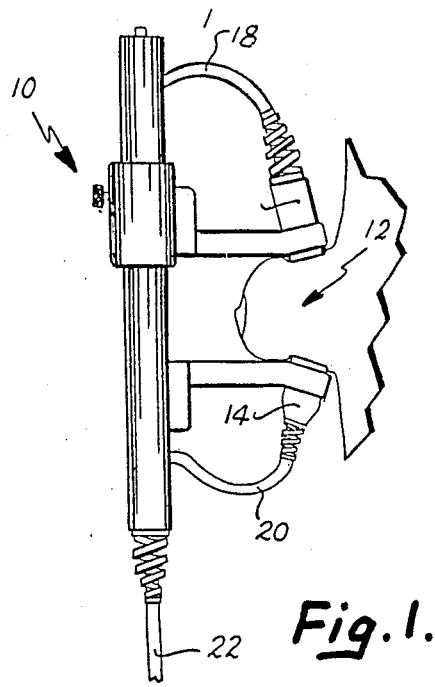
FIG. 1 is a fragmentary, pictorial side elevational view showing the general manner in which the optical examination instrument is utilized in obtaining optical response data from a given subject (here, the human breast) in accordance with Applicants' co-pending applications.

FIGS. 1 and 2 illustrate in a pictorial and generalized manner the basic aspects of the method and apparatus by which optical response data is preferably obtained for use in accordance with the invention, such method and apparatus being disclosed in detail in the aforementioned referenced and incorporated co-pending patent applications on behalf of Applicants. Somewhat more particularly, FIGS. 1 and 2 show the use of an optical "probe" 10 to examine (i.e., obtain optical response data from) a selected subject, in this case a human breast 12. In so doing, optical heads 14 and 16 of the probe 10 are lightly but firmly pressed against the top and bottom surfaces of the breast 12 sufficiently to provide good optical coupling, whereupon a sequence of light pulses of different wavelengths ranging over a selected spectrum is applied and the resulting intensity of the light energy infused into the breast is detected, preferably by both of the optical heads 14 and 16. As will be understood, the optical probe 10 is connected to a control console (not specifically illustrated) by cables 18, 20, and 22, by which suitable excitation (optical and/or electrical) is supplied and by which the optical response data is coupled to data-processing apparatus (e.g., a digital computer) located at the control console.

FIG. 2 illustrates the preferred placement and positioning of the optical heads during the overall examination, i.e., optical heads 14 and 16 are preferably moved sequentially to each of four different selected positions, designated by the numerals 24, 26, 28, and 30, respectively. Each such position constitutes a separate stage in the overall examination; i.e., the same sequence of selected light wavelengths is applied and resultant light intensity is detected at each of the four different locations. In the case of each breast (where breast examination is the particular application of the disclosed method and apparatus), examination positions 26 and 30 are generally aligned over the breast centerline, with position 26 being close to the chest wall and position 20 being remote from the chest wall, immediately behind the areola. One of the positions 24, 28 is thus disposed along the inner aspect of the breast while the other is disposed along the outer aspect.

As discussed at length in the referenced copending application Ser. No. 542,022 (now U.S. Pat. No. 4,570,638) of which the present application is a continuation-in-part, the optical response data produced in the general manner noted above thus consists of a sequence of electro-optical light-detector output values obtained at each of the different examination positions, each individual such detector output value comprising one individual point in the sequence of which it is a part, and corresponding to the amount of resultant light intensity detected at a particular examination location in response to the infusion of one particular wavelength (or narrow band thereof) in the applied spectrum. Generally speaking, these selected wavelengths comprise the visible and near-infrared spectrum extending approximately from 0.515 microns to somewhat beyond 1.2 microns and, as discussed more particularly below, this spectrum is preferably divided into on the order of about twenty to thirty specific examination wavelengths. As a consequence, the resulting optical response data corresponding to the light intensity received at each of the different examination locations comprises a corresponding sequence of electrical pulses comprising detector output magnitude values (which may be considered the "raw" data).

As further explained in the aforementioned copending application Ser. No. 542,022, now U.S. Pat. No. 4,570,638, the "raw" detector output data just noted, while constituting a quantified (i.e., numerically designated) value which could be compiled and graphically plotted, and studied in various ways, is nonetheless preferably "conditioned" in several particular ways before being presented in the graphic optical response "profiles" shown in the aforementioned co-pending application which is now U.S. Pat. No. 4,570,638, examples from which are also included in the drawings herewith, constituting FIGS. 3a, 3b, and 3c therein. In particular, two very significant "conditioning" factors are utilized, one of which is the particular separation distance between the two optical heads 14 and 16 which exists during each particular examination conducted. This dimension represents the "thickness" of the particular examination subject, and it is utilized with other known parameters (e.g., the "injected" or input light intensity and the "detected" or output light intensity received at a distant location on the examination subject) to compute the intensity reduction coefficient by use of the well-known exponential relationship expressing Beer's Law of intensity reduction across a given media thickness for a beam of light. This thickness or distance dimension is also (preferably) used to effect data conditioning by scattering and detector solid angle computation. Additionally, the optical response data is preferably further "conditioned" by in effect taking the ratio of the distance or thickness-conditioned data from a first light-receiver (e.g., one located at the optical head which also contains the light-emission apparatus, for example, optical head 16) with respect to the corresponding data from a second receiver (e.g., one which is located at the other optical head, i.e., head 14), which in the example shown is disposed at essentially the opposite side of the test specimen.

By so "conditioning" the raw detector output signals, a number of highly advantageous results are obtained, including the elimination of boundary effects (which, in the case of breast or other analogous examination, includes such skin characteristics or effects such as relative pigmentation, epidermal thickness, etc.), as well as in effect normalizing the data for the thickness of the particular examination subject. Accordingly, the resulting "conditioned" data is directly representative of intrinsic internal tissue composition and/or physiologic state, and it may be directly compared on a unit (i.e., numerical) basis to other such data, for example comparable data taken from other examination locations on the same breast (or other examination subject), or to data from the opposite such breast of the same patient, and indeed to data from totally different patients, with directly meaningful comparison results from which abnormalities and/or other characteristics may be discerned.

Accordingly, graphical "profiles" may thus be prepared from the resulting "conditioned" data to provide for highly meaningful comparison, and such profiles comprise the contents of FIGS. 3a, 3b, and 3c, which are repeated herein from Applicants' U.S. Pat. No. 4,570,638. In these figures, the different profiles in each horizontal row, designated "Inner", "Middle In", "Middle Out", and "Outer", respectively, correspond to optical response data obtained at the different examination positions 24, 26, 30, and 28, respectively (as illustrated in FIG. 2), and the vertical columns comprising FIGS. 3a, 3b, and 3c each represent different individual patients. Further, each individual graphical presentation or "profile" actually includes two superimposed traces, representing optical response data obtained at analogous positions on the two opposite breasts of the same examination subject, i.e., each such graphical representation constitutes a graphic contralateral comparison (as is also true of other such "profiles" shown in other figures and discussed hereinafter).

As may be observed from considering the different profiles of the three patients depicted in FIG. 3, as discussed above, particularly by contrasting the three different contralateral profile sets in any given horizontally aligned row thereof (representing the same examination location for each of the three different patients), vivid differences are clearly present and readily identifiable, on which diagnostic conclusions may be based. Nonetheless, in accordance with both the present invention and that of co-pending application Ser. No. 830,567, valuable and meaningful enhancements are disclosed for the treatment of the "conditioned" optical response data on which the patient profiles are based. For one thing, optical profiles such as those illustrated in FIGS. 3a, 3b, and 3c may be reformulated into different and more meaningful presentations, from the standpoint of emphasizing certain features or characteristics and making them more readily identifiable. This is accomplished, in the first instance, by replotting the data in a manner reversing the axis direction (sense) for the abscissa and, more significantly, by expanding the abscissa scale (at least in the areas of greatest plot variation), i.e., taking a larger number of wavelength-related optical response data samples (and sampling at particular selected discrete wavelength choices), and enlarging the abscissa scale so as to spread out the more-detailed data. Even more significantly (as more particularly discussed in co-pending application Serial No. 830,567, the data is preferably further conditioned prior to graphical presentation. Such further conditioning of the data is accomplished by accumulating and averaging the above-discussed conditioned optical response data from numerous different examination subjects for each of the individual points on the graphical presentations ("optical profiles" (each such point corresponding to the conditioned data value at a particular examination wavelength), and then using the resulting broad-based average values of wavelength-related data points by subtracting them from the corresponding conditioned current examination data values obtained during each new patient (or other subject) examination.

The subtractive procedure just noted has the effect of eliminating large, predominating, normative values for the wavelength-specific "conditioned" data and as a result amplifying or magnifying the remaining corresponding and related, but quite different, sequence of data values, which may then be graphically compiled and presented, or otherwise considered and evaluated. Further, the noted data cumulation and averaging may advantageously be carried out on the basis of chronological patient age groupings, such that the resulting "average" or "normal" data values which are subtracted from the conditioned examination values for a given subject are much more refined, and more specifically pertinent than would be true for a large "all ages" data base. Subtraction of these age-particular sets of conditioned data from the conditioned data of a particular individual under examination provides much more revealing data, from which a more revealing optical profile may be plotted, which is based upon age criteria and which is characterized primarily by specific departures from the norm or average for the age grouping of the particular examination subject being considered. Such data and corresponding profiles are, thus, highly representative of abnormality or eccentricity in the "intrinsic" internal tissue composition or state of the patient under examination.

The data base constituting such averaged values (whether on an age-related basis or otherwise) may and should be updated with each new patient or subject being examined, although it is to be noted that it is also desirable to eliminate from such data base the conditioned data (prior to the subtractive processing described above) for particular patients in which abnormalities are subsequently detected and proven, i.e., from patients having significant disease such as carcinoma which has been verified by subsequent diagnostic examination using such alternative media as mammography, ultrasound, and biopsy. Thus, the more the averaged data truly represents normative values, the more significant is the further-conditioned data brought about by the subtractive processing described above.

Figures 4, 4A, 4B, 4C, 4D:
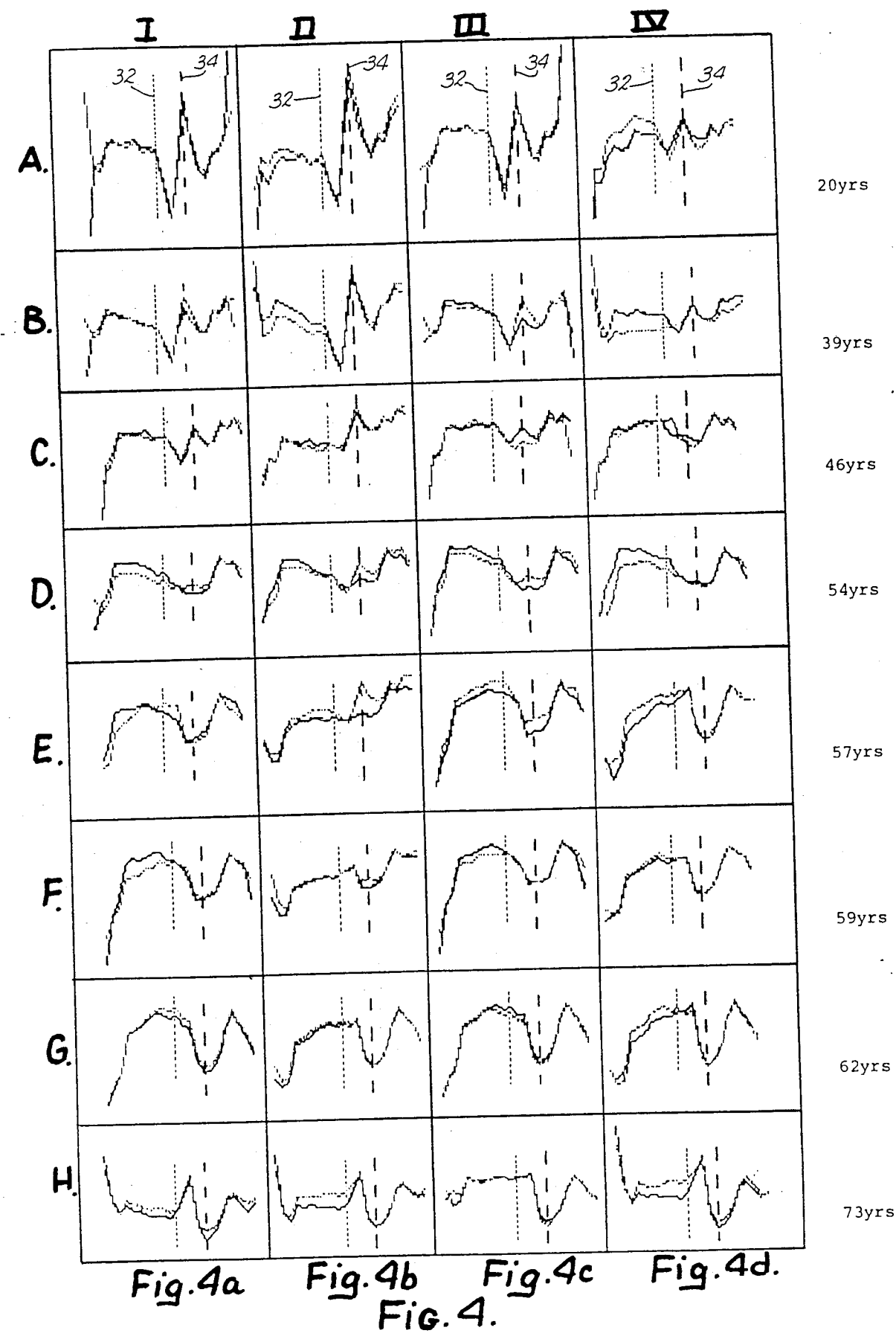
FIGS. 4a, 4b, 4c, and 4d are graphical presentations of optical profiles similar to those in FIG. 3, but based upon and incorporating refinements in accordance with Applicants' co-pending application Ser. No. 830,567.

The very substantial enhancements in optical profiles produced in accordance with the above-described further conditioning procedures may be appreciated by studying the content of FIG. 4, bearing in mind that the vertical columns of profiles in FIG. 4 compare to the horizontal rows of profiles in FIG. 3 (both designated by the numerals I-IV, inclusive); however, it must also be borne in mind that the graphical profiles of FIG. 3 are merely illustrative of randomly-occurring individual examination subjects, which include non-typical or anomalous physiological characteristics, whereas the profiles shown in FIG. 4 represent the averages of numerous "typical", or "normal", subjects. Of course, the four different sets of profiles in each horizontal row of FIG. 4 (designated "A", "B", etc.) represent each of the four different examination locations, and all of the profiles in each different horizontal row (of FIG. 4) correspond to a particular chronological age grouping for the associated patients or subjects (indicated in the right-hand margin of the figure).

Referring more particularly to the "average", or normative, profiles of FIG. 4, it is to be noted that profile includes a pair of mutually-spaced, vertically-disposed reference index lines designated by the numerals 32 and 34, portrayed by a series of dots in the one instance (index 32) and a series of dashes in the other instance (index 34). In each vertical column of profiles, index lines 32 and 34 are disposed in vertical alignment with one another, so that the reference points on the corresponding profiles from one horizontal row to another in a vertical column may readily be discerned and contrasted. Bearing this in mind, one may readily come to appreciate the information content present in the profiles of FIG. 4, both from the standpoint of the different examination locations of a given "average patient" at a given point in time, as well as from the standpoint of the same examination location for "average patients" of differing ages, considering each vertical column as proceeding (from top to bottom) in accordance with advancing chronological age. Accordingly, each of the different columns in FIG. 4, and in fact the entire figure as so construed, essentially characterizes in a direct, graphic manner, normative breast physiology changes which occur throughout a life cycle from 20 years of age to 73 years of age.

Figures 5A, 5B, 5C, 5D:
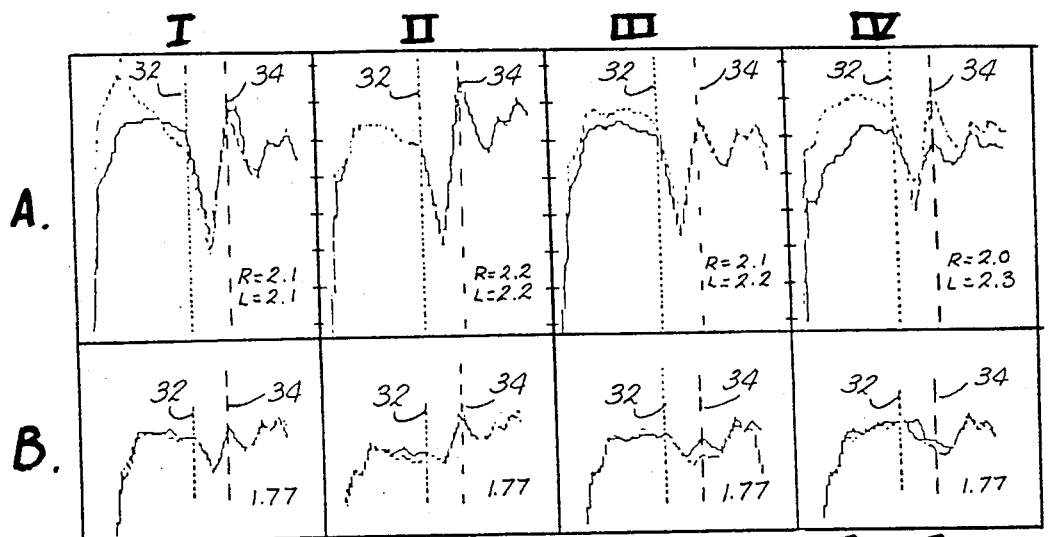
FIGS. 5a, 5b, 5c, and 5d are each two-part graphical presentations of optical response data of the general nature as that shown in FIG. 4, but depicting a "normal" response in juxtaposition to an "abnormal" response in comparable chronological age groupings.
Figures 6A, 6B, 6C, 6D:
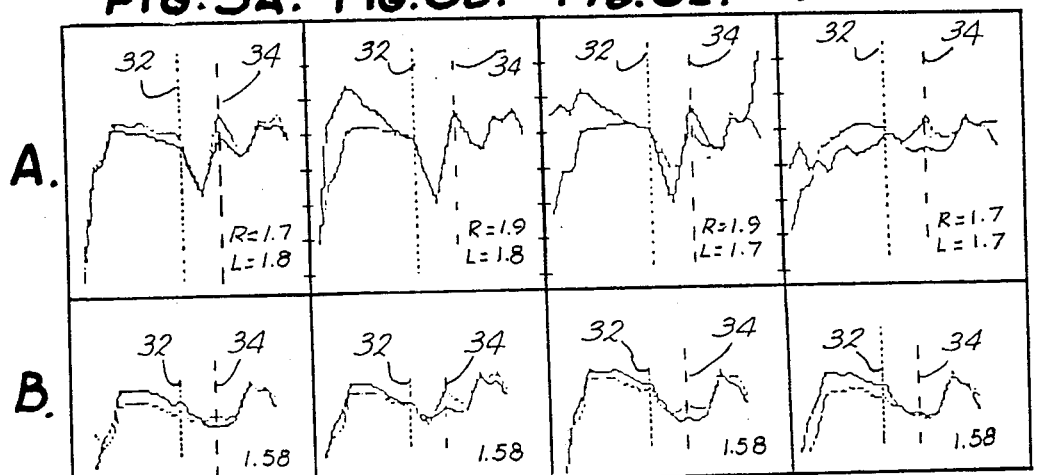
FIGS. 6 and 7 are graphical presentations similar to those of FIG. 5, but depicting different subjects in different age groupings.
Figures 7A, 7B, 7C, 7D:
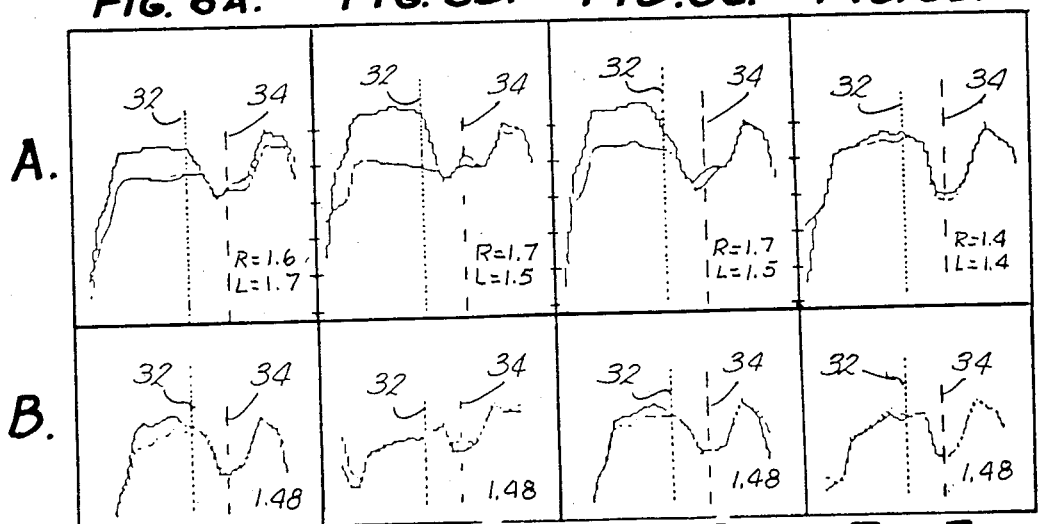

With the above factors and criteria in mind, consideration of FIGS. 5, 6 and 7 will further exemplify the significance and usefulness of those aspects of Applicants' discoveries described above. These figures have the same general arrangement as FIG. 4, i.e., the four vertical columns "I, II, III, and IV" characterize the different examination locations as referred to above (illustrated in FIG. 2) and each of the individual profiles comprise two superimposed traces which separately characterize the two breasts of each patient; however, each of the three horizontal rows designated "A" are optical profiles taken from three different particular patients or examination subjects aged 47, 53, and 59, respectively, and the three horizontal rows designated "B" represent "normal" (actually, average) optical profiles (like those in FIG. 4) representative of subjects of essentially the same chronological age as the subjects in corresponding rows "A". By comparing the shape of these correspondingly-displayed optical profiles (i.e., comparing the "A" and "B" profiles of FIGS. 5a, 5b, 5c, etc.), one may note many specific differences and variations. These differences are highly significant indicia which are rendered meaningful, and understandable, in accordance with Applicants' discoveries, and are discussed more comprehensively in co-pending application Ser. No. 830,567, (incorporated herein by reference) to which the reader is referred for more detail.

For purposes of the present disclosure, which is basically directed toward other attributes of the underlying technology, it may be noted that, with respect to FIG. 5, the contour and characteristics of the plots, together with the contralateral asymmetry (i.e., shape differences between the two traces of an individual profile), indicates considerably more glandular and fibrous tissue, as well as more vascularity, than one should expect for this age grouping, indicating definite risk probability (anomaly). Clinical medical examination of this patient validated these conclusions by diagnosing the presence of ductal hyperplasia, with bizarre calcification in the upper outer quadrant of the left breast, together with several large cysts. Biopsy showed intraductal carcinoma of the left breast. The optical profile for patient "A" of FIG. 6 shows a generalized condition of lack of the normal fatty replacement of glandular tissue (as indicated in the FIG. 6 "B" profiles), with substantial contralateral asymmetry in the area to the left of index 32, where the plot for one breast appears to show significant hemoglobin increase, indicative of increased blood supply to the area. Medical evaluation of this patient confirmed the presence of anomaly, but characterized it as "apparently benign", with calcifications at the center of the right breast; however, ensuing biopsy confirmed the presence of intraductal carcinoma of the right breast. In FIG. 7, the foregoing criteria again indicates seemingly evident anomaly, including substantially increased vascularity suggestive of widely-distributed malignancy in the right breast, and both medical examination and biopsy verified this indication by confirming extensive and widespread carcinoma of the right breast without the presence of any specific large mass (tumor).

Notwithstanding the evident significance of graphical plot interpretation, such as is generally discussed above, made possible through the "optical profiles" noted (and discussed in more detail in co-pending application Serial No. 830,567, Applicants have additionally provided further novel and highly useful refinements of the underlying concepts, in accordance with which the conditioned data plotted into the optical profiles discussed above is subjected to other and different processing, based upon methodologies set forth hereinafter and illustrated by FIGS. 8-13, inclusive, in accordance with which automated, non-subjective, and accurately-repetitive machine analysis may be accomplished, and corresponding conclusions obtained, by use of programmable processes which address the conditioned data apart from any graphical presentation thereof.

More particularly, it will be appreciated that each of the points graphically plotted in the optical profiles, as discussed above, has a particular numerical value which, while arbitrary in an absolute sense, is nonetheless highly meaningful in a relative sense. Accordingly, the data in the different optical profiles lends itself to substantial processing possibilities and procedures. One such procedure is to compute a numerical First Moment (i.e., average) magnitude for each patient profile, and/or for each of the two individual traces plotted in such profiles, as depicted for example, in FIGS. 5-7. Similar but somewhat broader averages, or First Moments, may be prepared for use as a comparison basis, computed from the combined (averaged) conditioned optical response data representative of a large number of age-grouped patients who have undergone examination, as for example are plotted in FIG. 4; for example, such First Moments may be computed on the basis of each "view", and/or of all "views" (examination locations on the subject) and for either or both breasts, in any given age grouping (or for that matter for all ages).

Figure 8:
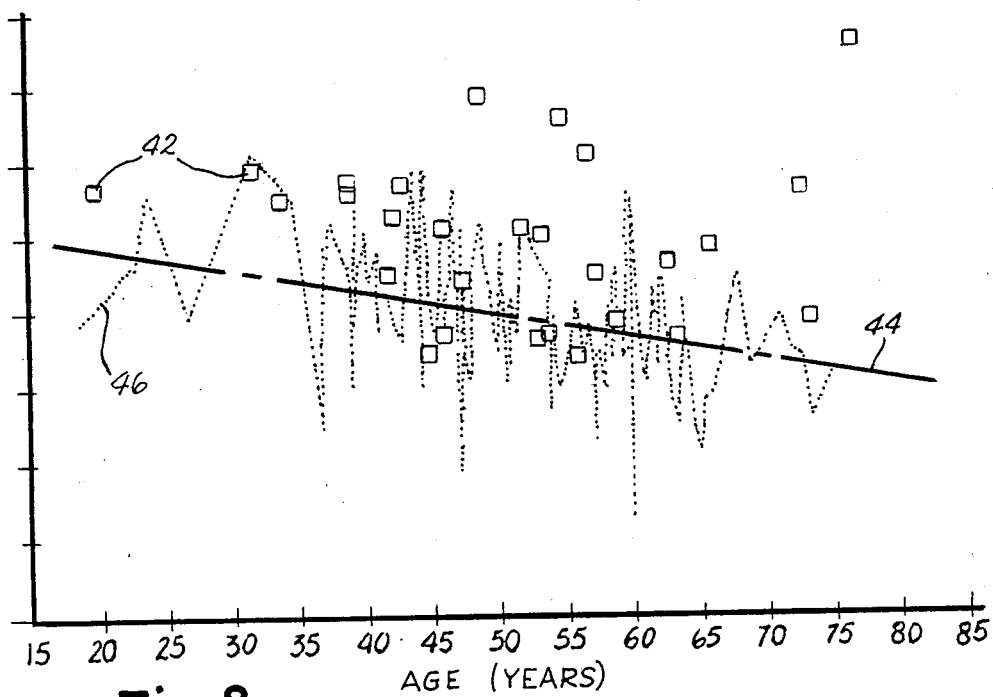
FIG. 8 is a graphical presentation (plot) showing certain conditioned optical response data plotted with respect to age.

FIG. 8 presents a plot of certain First Moment values for individual patients (all views, both breasts) as a function of patient age (age being the abscissa), taken from a data base of over one hundred "non-CA" (i.e., non-carcinogenic) cases. Superimposed upon this plot is a series of analogous data points 42 (highlighted by a dark enclosing rectangle), each of which represents one of twenty-nine cases determined to be "suspicious by mammography" with respect to carcinoma. The relative position of these "suspicious" cases upon the plotted field clearly portends analytic significance, and this is particularly true considering the fact that of the twenty-nine "suspicious" cases a certain number will or may prove to be benign. Thus, the center of gravity of the multiple-point "non-CA" trace 40 in FIG. 8, as represented by the heavy line 44, clearly trends downwardly with age, and by far the greater proportion of the "suspicious" case data points 42 lie above the center of gravity line 44.

Accordingly, it seems reasonable to believe from FIG. 8 that at least an initial, but nonetheless meaningful, diagnostic data-interpretation process which could be implemented by programmed apparatus could be provided by obtaining a comparable First Moment or average magnitude (all views, both breasts) for a given patient under examination, based upon the conditioned optical response data for that patient, and contrasting that First Moment magnitude with the position of the center of gravity line 44 at the age for that particular patient. Indeed, based upon the data presented in FIG. 8 (which is no doubt insufficient for final conclusions), one would conclude that even such a preliminary machine-based readout might provide a degree of certainty as high as about 75 percent, since approximately that percentage of the "suspicious" points 42 lie above the center of gravity line 44 in FIG. 8. Regardless of such speculation, the underlying methodology appears clearly validated by the graphical study of FIG. 8, particularly when one remembers that the trace 40 is based upon a combination of all examination views or locations and both breasts; quite clearly, as demonstrated by the discussion of FIGS. 5, 6 and 7 above, other First Moment data points based upon the conditioned data for separate breasts would be very likely to provide improved accuracy, as would analogous data points for each separate examination view or location on each separate breast. Of course, the particular parameters of the center of gravity line 44 are likely to be increased in accuracy in direct proportion to increasingly large population studies.

In demonstration of the basic diagnostic process, or technique, referred to just above with respect to FIG. 8, generalized (but relatively accurate) optical data resolution numbers (i.e., optical data First Moment magnitudes for each breast profile, or trace, in each view) are denoted on each of the different profiles presented in each row "A" of FIGS. 5, 6, and 7 ("R" referring to right breast and "L" to left). Overall First Moment values (all views, both breasts) on an age-specific basis are presented in the comparison profiles shown in each row "B" of these figures. It is believed that the mere initial comparison of such magnitudes on a view-byview basis clearly demonstrates the usefulness and desirability of such a procedure, since the departures from the norm are so apparent in and of themselves and since they compare so favorably with the analytical observations set forth above in the discussion of FIGS. 5, 6, and 7, based upon graphical plot comparisons as well as comparing favorably with the actual medical diagnoses noted there.

Figure 9:
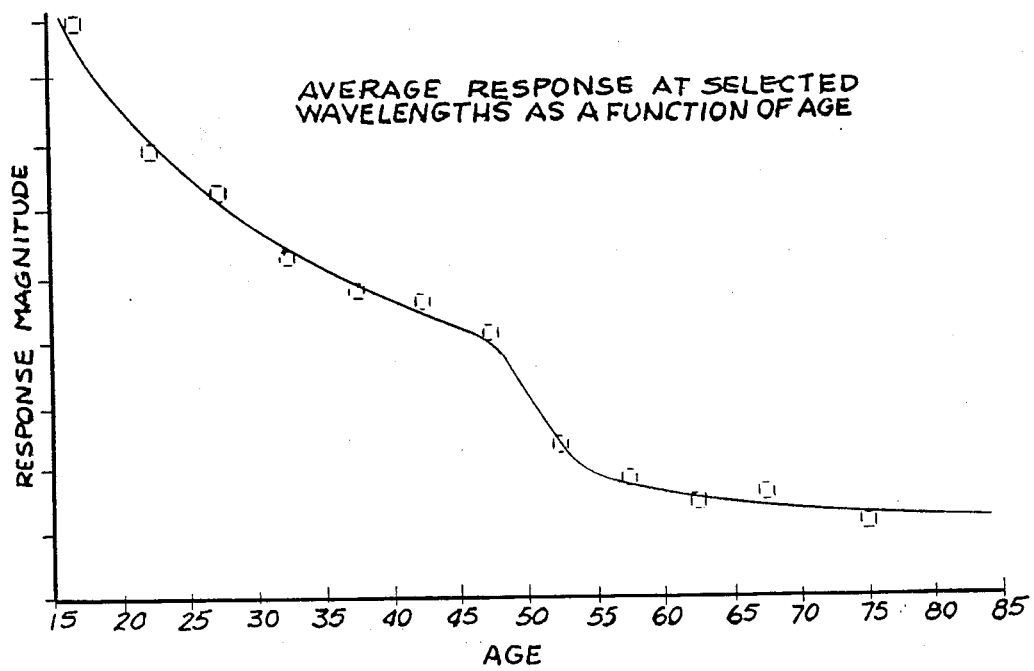
FIG. 9 is another graphical presentation (plot) showing other conditioned optical response data plotted with respect to age.

A further and in some ways even more significant illustration of the information content in the conditioned optical data is contained in FIG. 9, which is included to provide additional information on which to base a more complete apprehension of, and appreciation for, the present invention. FIG. 9 comprises a plot of the conditioned optical response data produced at a particular selected light wavelength band (e.g., from about 0.10 microns to about 0.990 microns), i.e., the wavelengths encompassing index line 34 of FIG. 4, for all views of a number of different examination subjects, plotted with respect to age. As will be apparent, the basic shape and overall disposition of this plot corroborates the center of gravity 44 of the plot in FIG. 8; however, the extent to which the particularized data of FIG. 9 actually does represent ongoing metabolic characteristics is believed clearly evidenced by the prominent "knee" in the curve, which is located directly at the chronological age group where menopause typically occurs, testifying to a corresponding and notable decrease in the presence of glandular breast tissue. Further, it will be noted that the degree of downward curvature of this plot (FIG. 9) is much more pronounced above the "knee" than below it, indicating a continual and progressive largerscale decrease in glandular tissue prior to menopause, a precipitate decrease during the menopausal years, and only very slow such change thereafter, when the process of glandular atrophy and fatty replacement has been largely completed (corresponding directly to the progressions graphically displayed in FIG. 4). Clearly, FIG. 9 also demonstrates a basis for a potentially advantageous procedure for automated diagnoses based upon the conditioned optical response data in accordance with Applicants' invention.

Figure 10:
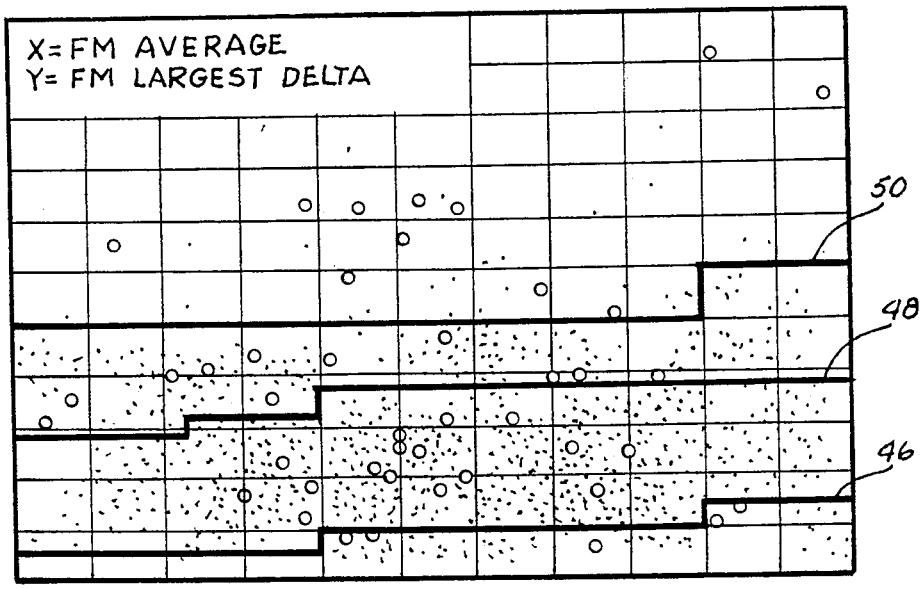
FIG. 10 is a different form of plot showing a distribution of a large population of conditioned optical response data, subdivided in accordance with certain statistical characteristics.

Notwithstanding the basic and essential usefulness of the approaches referred to above in conjunction with FIGS. 8 and 9, further and additional such approaches have been explored and are now described, for augmenting and extending the accuracy and usefulness of the investigative processes generally under consideration. One rather significant such approach is illustrated in FIG. 10, which constitutes a plot of certain data somewhat similar to that presented in FIG. 8 but representing a large population shown in unconnected scatter form. Thus, each of the small dot-like points in FIG. 10 presents certain conditioned optical data (to be described more specifically hereinafter) which represents a single individual in a large data base comprised of subjects not known to have present carcinoma. The large dark dots in this figure represent analogously-conditioned optical response data, but characterize biopsy-positive carcinoma cases, plotted similarly.

While it might at first appear that there is substantial dispersal of the large carcinoma-indicative dots throughout the field of the small non-carcinoma-indicative dots in FIG. 10, careful analysis shows the contrary. That is, as the field-dividing dashed boundary lines 46, 48, and 50 help to reveal, several distinctly different areas (subsets) may be discerned within the overall field of FIG. 10, with each of the different such areas characterizing significantly different probability subsets. First, the highest probability (of finding cancer relative to not finding it) lies within the field defined above boundary line 50, which in fact contains a ratio of approximately 29 percent biopsy-proved carcinoma cases. The second such field comprises the divided area located between the abscissa and boundary 46, and between boundaries 48 and 50, which are comparable areas characteristic of about 11 percent biopsy-proved carcinoma cases. Within the field between boundary lines 46 and 48, the probability falls to approximately 2.6 percent. The ratio for the entire plot is 5.4 percent (which, of course, is substantially greater than the probability existing for the general population as a whole). Clearly, the resulting usefulness of analysis such as that utilized in arriving at the plot in FIG. 10 appears to be abundantly demonstrated.

The actual conditioned optical response data plotted in FIG. 10 comprises the magnitude produced by taking the difference between the First Moment values ("FM Delta") for each breast in each of the different examination views (as discussed above and as illustrated by the aforementioned numerical values indicated in rows "A" of FIGS. 5, 6, and 7), and comparing (plotting) such difference with the average value of all such First Moment magnitudes (illustrated by the numerical values indicated in rows "B" of such figures). This relationship (this difference between the specified First Moment magnitudes) is referred to herein at "Criterion A".

A number of additional such criteria, i.e., specified analytic relationships, are also defined in accordance herewith, including the following:

First Moment range, assigning a negative value if high and low values are in opposite breasts, plotted against patient age ("Criterion B");

Largest difference between First Moment magnitudes occurring between wavelengths from about 0.7 microns to about 0.85 microns, versus the average value of the First Moment per se ("Criterion C");

Largest difference in First Moment between same examination views, versus patient age ("Criterion D");

Largest difference between First Moment magnitudes in the same views occurring between wavelengths of about 0.7 microns to about 0.85 microns, versus largest absolute difference between First Moment magnitudes from any one examination view to any other such view (for the same patient) ("Criterion E");

Average First Moment magnitude occurring between wavelengths of about 0.7 microns to about 0.85 microns in any view, versus average value of First Moment ("Criterion F");

Largest difference in Second Moment magnitudes in any one view versus average of the RMS (root means square) differences between views ("Criterion G");

Largest difference in the same view between conditioned optical response data obtained between wavelengths of about 0.65 microns to about 0.85 microns, normalized to the three other differences noted above, versus patient age ("Criterion H"); and Largest difference between conditioned optical response data values occurring in any view between wavelengths of about 0.85 microns minus comparable magnitudes obtained at wavelengths of about 0.80 microns, plus magnitudes occurring within the range of about 0.7 microns to about 0.85 microns, versus average value of First Moment (for that view) ("Criterion I").

As will be understood, the "Second Moment" referred to above comprises the value of the square root of the average of the squared values of each of the conditioned optical response data points, and the "RMS" value is the square root of the sum of the squares of the magnitude of such data points.

Each individual plot representative of one of the above-stated criteria provides meaningful risk percentage definition information, it is believed, although each such plot is not regarded as having the same relative degree of importance in arriving at an ultimate such conclusion. Consequently, what is required is a weighted programmatic solution which takes each such evaluative procedure into consideration and provides a corresponding "ultimate" answer (whose actual ultimate accuracy is, of course, a function of the underlying assumptions made in weighting the multiple averaging process to be used). Of course, many specifically-differing such weighted solutions may be contemplated, and it remains to be seen which particular such approach ultimately proves to be the most accurate. On a provisional basis, however, one useful such resolution program, included basically for purposes of illustration, is as follows: accord a comparatively high number (on any given numerical scale, say from one to ten) to patients in a comparatively high percentile of risk category (for example, that graphically portrayed in FIG. 10), with fractional points added if that same examination subject is also present in other lower-risk subsets. A significant positive numerical addition should be added if the subject is, additionally, found present in a risk-indicative subset considered somewhat orthogonal to the initially-noted subset (as for example due to having a number of other and different biopsy-positive carcinoma patients within defined categories). Also, values should be subtracted if the examination subject is found in any of the comparatively low-percentage risk subsets, and if that subject is not present in any of the defined subsets, as noted above, an overriding characterization of low risk could peremptorily be assigned.

As stated above, the particular weighting factors to be used in such an all-encompassing weighted-average resolution program are subject to substantial variation, and the choice no doubt involves considerable difficulty if true optimization is actually to be envisioned. Nonetheless, the generalized usefulness of such a resolution program has been demonstrated, and the general format described above has in fact been followed in producing specific results from a data base numbering a total of 819 examination subjects, comprised of two main groups, i.e., biopsy-positive carcinoma cases, numbering 44 in total, and all others, numbering 775. Two subsets of the latter group may be separated out and used for separate scoring, namely, biopsy-negative subjects (numbering 66) and "asymptomatic" cases (numbering 106). The results obtained by use of the aforementioned resolution program on this data base are set forth in Table I below, and, illustrated in FIGS. 11, 12, and 13, discussed below.

Figure 11:
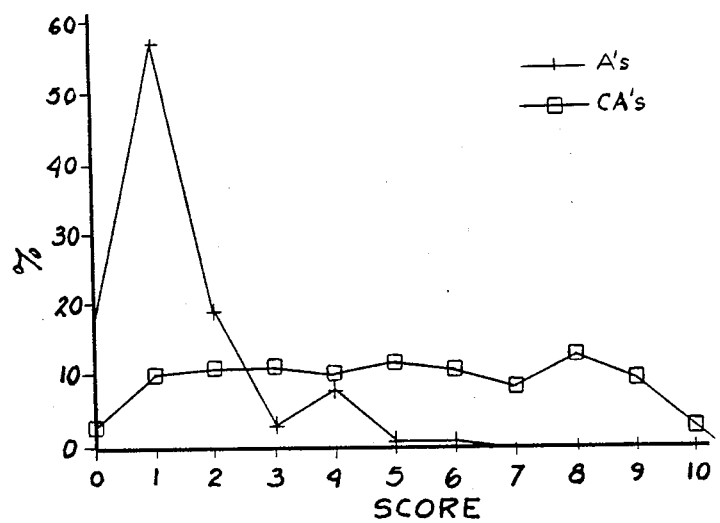
FIGS. 11, 12 and 13 are plots of scoring distributions for selected examination subject populations, generally demonstrating efficacy of the subject methodology.
Figure 12:
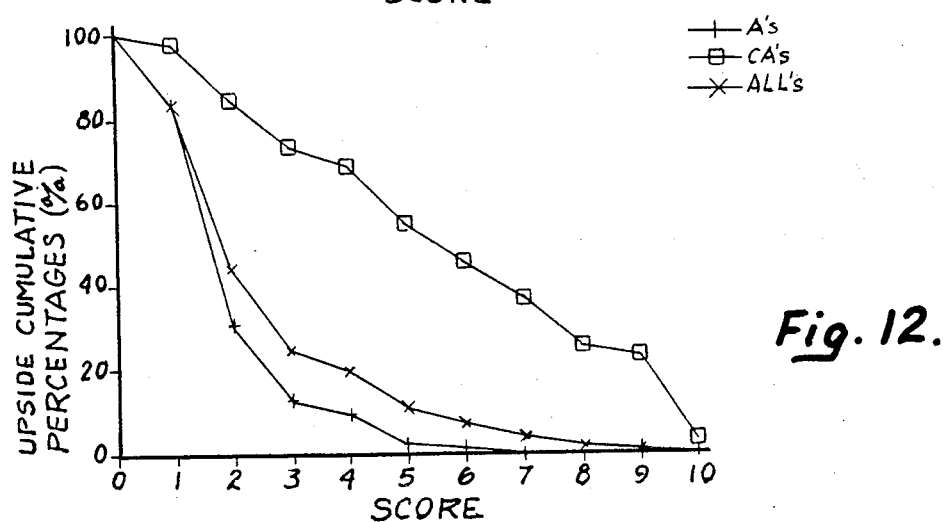
Figure 13:
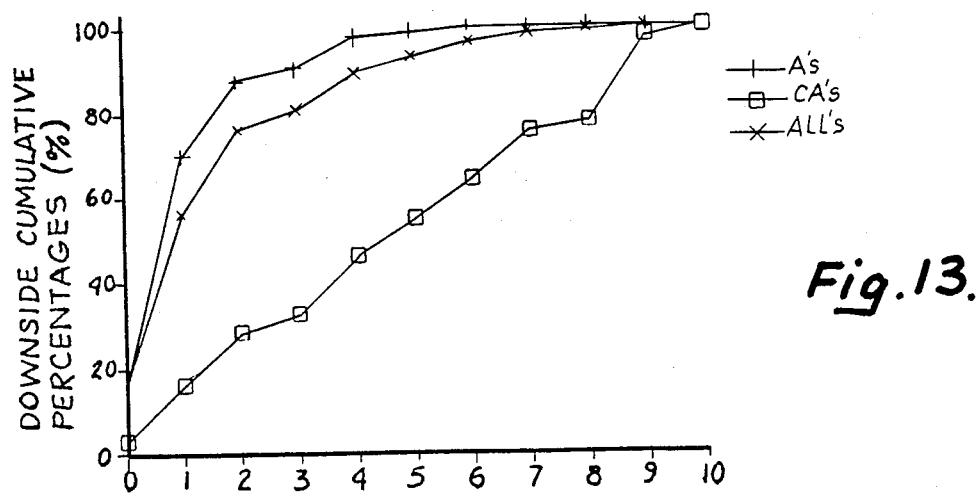

In considering Table I and FIGS. 11–13, inclusive, it should be borne in mind that the data base overall was skewed toward examination subjects having, or likely to have, carcinoma or other breast anomaly, since the entire population comprised women referred for mammography for one reason or another, most often because of exhibiting at least some clinical symptoms. The fact that this overall data base did in fact include 44 cases of biopsy-proved carcinoma is further evidence of this population skew, indicating an overall carcinoma probability of 0.11, whereas the generally-established probability for the U.S. population at large is some forty times less than that. The subset defined as "asymptomatic", referred to above, was selected on the basis of clinical histories showing mammography referral merely for "base line" or "routine" purposes, rather than specific assigned risk; nonetheless, even within this subset there may of course be suspect cases who were simply not designated as such, for any of a variety of possible reasons.

Table I, set forth below, summarizes in tabular form the general scoring (on a scale of 0–10) produced by the above-described data resolution program or process with respect to the data base described, on the basis of the four groups identified (including the two subsets). With reference to this Table, it may be seen that, arbitrarily putting all subjects with scores equal to two or less in a designated "low-probability" population, and placing all examination subjects with a score greater than two in a "high-probability" population, it may be observed that some 88 percent of the subjects thought to be asymptomatic fall in the "low-probability" population, while only 27 percent of the biopsy-positive cases fall into such group; conversely, 73 percent of the biopsy-positive cases fall into the "high-probability" group, and only 12 percent of the ostensibly asymptomatic population fall into the "high-probability" population. Bearing in mind the abovenoted skewing of the data base itself, the accuracy of the data resolution program or process under discussion clearly seems likely to possess even greater accuracy when applied to the general population. Further, the fact that Table I shows several relatively high scores (e.g., one "4" and three "3", in the "low-probability" population may well be indicative of the fact that the optical response process itself differentiates many different types of physiologic anomaly apart from carcinoma per se, e.g., fibroadenoma), indicating the possibility that, in use as a general screening instrumentality, the optical response methodology may well possess truly surprising potential. That is, considering the data set forth in Table I from another perspective, a patient thought to be asymptomatic who is classified in the high-percentage risk category (scores of 3 or above) may well have an unsuspected probability of actually having carcinoma or other undesirable anomaly, since that likelihood is more than twenty times greater than the risk probability for a different asymptomatic patient who is classified by the procedure in the "low-probability" category. Further, the likelihood of carcinoma presence in asymptomatic patients classified in the "low-probability" area is only 30 percent that of the entire asymptomatic subset, while the actual probability of asymptomatic patients classified in the "high-probability" category is approximately six times that of the average patient.

TABLE I

SCORING SUMMARY

| Score | Biopsy-Positive (CA's) | | Biopsy-Negative (N's) | | No Symptoms (A's) | | Not Biopsy-Positive (All's) | |
|---|---|---|---|---|---|---|---|---|
| 0 | 1 | | 10 | | 17 | | 132 | |
| 1 | 6 | | 28 | | 57 | | 298 | |
| 2 | 5 | 27% | 10 | 73% | 19 | 88% | 150 | 75% |
| 3 | 2 | | 3 | | 3 | | 36 | |
| 4 | 6 | | 3 | | 8 | | 68 | |
| 5 | 4 | | 2 | | 1 | | 28 | |
| 6 | 4 | | 4 | | 1 | | 25 | |
| 7 | 5 | | 0 | | 0 | | 17 | |
| 8 | 1 | | 3 | | 0 | | 15 | |
| 9 | 9 | | 2 | | 0 | | 6 | |

TABLE I-continued

| | SCORING SUMMARY | | | |
|---|---|---|---|---|
| Score | Biopsy-Positive (CA's) | Biopsy-Negative (N's) | No Symptoms (A's) | Not Biopsy-Positive (All's) |
| 10 | 1  73% | 1  27% | 0  12% | 0  25% |
| Totals: | 44 | 66 | 106 | 775 |

The validity of the methodology described above is believed self-apparent, especially in view of the results shown in Table I. Further confirmation is provided in FIGS. 11-13, however, of which FIG. 11 graphically depicts the significant difference between asymptomatic patients ("A"s) and biopsy-positive patients ("CA"s) with respect to weighted score. FIGS. 12 and 13 illustrate cumulative upside percentages and cumulative downside percentages, respectively, with respect to weighted score, for asymptomatic patients, biopsy-positive patients, and all patients ("ALL"s). Thus, in accordance with these presentations, cumulative percentages such as those discussed briefly above may readily be located for any given weighted score, the clearly-evident extent of difference between the biopsy-positive cases and the non-biopsy-positive cases ("ALL"s) additionally establishing the validity of the underlying methodology.

As noted at various points above, the methodology of the invention is discussed and presented largely in conjunction with human breast examination but is for no reason specifically confined to that particular area of inquiry. On the contrary, the methodology is also believed to be applicable, to a substantially equivalent degree, to other human organs and tissue masses or extremities, as well as to comparable non-human subject matter. Indeed, while the usefulness of the methodology on an in vivo basis has evident and even surpassing value, there is no particular reason to believe that the underlying methodology is in fact less useful when conducted on other bases (e.g., on tissue samples, etc.), and in the last analysis it is likely to be directly applicable to essentially any biological or organic material or the like which is transmissible by optical radiation of the general type described.

It is to be understood that the above detailed description is but that of one exemplary preferred embodiment of the invention, and that numerous changes, alterations and variations may be made without departing from the underlying concepts and broader aspects of the invention as set forth in the appended claims, which are to be interpreted in accordance with the established principles of patent law, including the doctrine of equivalents.

The embodiment of the invention in which an exclusive property or privilege is claimed are defined as follows:

1. A method of assessing the internal physiological compositional state of an individual examination subject comprised of organic matter and the like which is transmissible by at least certain selected light energy wavelength spectra, comprising the steps: applying the selected light energy spectra to said examination subject in a manner which infuses at least certain of such light into the interior of such subject; detecting the presence of said infused light after the same has transmissed a particular distance defining at least a portion of the interior of said examination subject; quantifying the detected light energy for said examination subject as a sequence of values correlated with at least certain of said selected wavelengths to thereby produce a sequence of discrete wavelength-related values for said examination subject; conditioning said discrete values at least partially on the basis of said distance, to produce a series of wavelength-related individual conditioned quantified values particularizing the said individual examination subject; determining at least one composite averaged value from said series of different wavelength values, to characterize the particular subject under examination in terms of at least one individual numerical value; and comparing selected ones of said at least one numerical value to other analogously-obtained individual numerical values to thereby assess the internal physiological compositional state of the subject under examination in relation to that characterized by said other numerical values.

2. The method as set forth in claim 1, wherein said step of determining an averaged value from said series of values for the individual examination subject comprises determination of the statistical first moment of the individual wavelength-related values in said series.

3. The method as set forth in claim 1, wherein said step of determining an averaged value from said series of values for the individual examination subject comprises determination of one or more of the group consisting of the statistical first moment of the individual wavelength-related values in said series, the statistical second moment of such individual values, and the root-means-square of said series of values.

4. The method as set forth in claim 1, including the steps of applying said light energy spectra to said examination subject at a plurality of different selected locations thereupon; detecting, quantifying and conditioning resulting infused light for each such different location, to produce a series of wavelength-related conditioned quantified values for each of said plurality of different examination locations on each examination subject; and determining an averaged value from each of said plural series of values to provide a corresponding plurality of said averaged values, said plurality of averaged values collectively characterizing the particular subject under examination.

5. The method as set forth in claim 4, wherein at least certain of said averaged values in said plurality thereof comprise the statistical first moment values of a particular one of the series of values in said plurality thereof.

6. The method as set forth in claim 4, wherein said averaged values in said plurality thereof comprise one or more of the group consisting of the statistical first moment, the statistical second moment, and the root-means-square of the series of values on which it is based.

7. The method as set forth in claim 1, wherein said other analogously-obtained individual numerical values comprise at least one broad-based average made from a plurality of series of conditioned quantified values produced by substantially identical light-spectra examination of a plurality of individual examination subjects.

8. The method as set forth in claim 7, wherein said at least one broad-based average is made from a plurality of value series each of which corresponds to an examination subject within a chronological age classification comprising the approximate chronological age of the individual subject being examined.

9. The method as set forth in claim 8, including the steps of preparing a composite averaged value series from said plurality of series which correspond to examination subjects classified by chronological age, and using said composite average data set as a basis for assessing the internal state of the individual subject under examination.

10. The method as set forth in claim 9, including the step of preparing an individual numerical value by averaging the values in said composite value series.

11. The method as set forth in claim 10, wherein said step of preparing an individual numerical value comprises determining the statistical first moment of the values comprising said composite value series.

12. The method as set forth in claim 10, wherein said step of preparing an individual numerical value comprises determining one or more of the group consisting of the statistical first moment, the statistical second moment, and the root-means-square of the values comprising said composite value series.

13. The method as set forth in claim 12, wherein said stop of determining an averaged value from said series of values for the individual examination subject comprises determination of one or more of the goup consisting of the statistical first moment of the individual values in said series, the statistical second moment of such individual values in said series, and the root-means-square value of said individual values in said series.

14. The method as set forth in claim 13, wherein said step of comparing selected ones of said one or more individual numerical values for the individual examination subject to said other individual numerical values comprises the preparation of a weighted average which is based upon and which incorporates as unequal components at least two of the members of each of said groups.

15. The method as set forth in claim 1, wherein said step of determining at least one averaged value from said series of values comprises the determination of a plurality of statistically-based individual numerical values derived from said values in said series, and wherein said step of comparing selected ones of said individual numerical values to other analogously-obtained individual numerical values comprises the steps of preparing a weighted average which is based upon and which incorporates at least two of said plurality of statistically-based individual numerical values derived from the values of said series and at least two of a plurality of analogous numerical values based upon data characterizing a defined grouping of typical and normative examination subjects.

16. The method as set forth in claim 15, wherein said step of preparing a weighted average comprises unequally combining said at least two of said plurality of statistically-based individual numerical values derived from the values in said series and said at least two of a plurality of analogous numerical values are based upon data characterizing a defined grouping of typical and normative examination subjects.

17. A method of assessing the internal physiological compositional state of an individual examination subject comprised of organic matter and the like which is transmissible by at least certain selected light energy wavelength spectra, comprising the steps: applying the selected light energy spectra to each of a plurality of examination subjects including said individual examination subject, in a manner infusing at least certain of such light into the interior of each such subject; detecting the presence of said infused light at a location on each such subject which is spaced from that where the light energy was applied by at least the thickness of the light-infused portion of said subject; quantifying the detected light energy for each examination subject as a sequence of values correlated with at least certain of said selected wavelengths to thereby produce a sequence of discrete wavelength-related values for each such examination subject; conditioning said discrete values for each such examination subject at least partially on the basis of said thickness, to produce a series of individual conditioned quantified wavelength-related values for each such examination subject; determining at least one composite averaged value from a plurality of the different series of wavelength-related values which pertain to at least some of said plurality of examination subjects to characterize a reference averaged value; determining at least one other averaged value from the series of wavelength-related values pertaining to said individual examination subject; and comparing said at least one reference averaged value with said at least one other averaged value to thereby assess the internal physiological compositional state of the individual subject under examination in relation to that characterized by said reference average value.

18. The method as set forth in claim 17, including the steps of applying said light energy spectra to said examination subjects at a plurality of different selected locations with respect thereto; detecting, quantifying and conditioning resulting infused light for each such different location, to produce a series of wavelength-related conditioned quantified values for each of said plurality of different examination locations on each examination subject; and determining an averaged value from each of said series of values to provide a plurality of said averaged values, certain of said plurality of averaged values collectively characterizing said plurality of examination subjects and certain of said plurality of averaged values collectively characterizing said individual examination subject; and comparing at least certain of said plurality of averaged values which characterize said individual examination subject with at least certain of said plurality of averaged values which characterize said plurality of examination subjects to thereby assess the internal state of the individual examination subject.

19. The method as set forth in claim 18, wherein said step of comparing is carried out on the basis of one or more of the relationships in the group consisting of Criteria A-I, inclusive.

20. The method as set forth in claim 19, wherein said step of comparing includes the step of preparing an evaluation score based upon a cumulation of weighted values which are representative of the application of said one or more of the relationships in said group of Criteria.

21. The method as set forth in claim 20, wherein said step of preparing an evaluation score is based upon a cumulation of unequal values which are each representative of the application of a particular one of said one or more relationships in said group of Criteria.

22. The method as set forth in claim 21, wherein said step of preparing a weighted cumulation of values is carried out by using program-controlled apparatus which has been programmed to carry out a predetermined value-weighting schedule representative of the application of said one or more relationships in said group.

23. The method as set forth in claim 22, wherein said step of preparing an evaluation score based on a cumulation of weighted values is carried out by programming said apparatus to accord a comparatively high number to patients in a comparatively high percentile of risk category, to add fractional points if that same examination subject is also present in other lower-risk subsets, to add a significant positive numerical addition if the subject is, additionally, found present in a risk-indicative subset considered somewhat orthogonal to the initially-noted subset, to subtract values if the examination subject is found in any of the comparatively low-percentage risk subsets, and if that subject is not present in any of the defined subsets to peremptorily assign an overriding characterization of low risk.

24. The method as set forth in claim 21, including the step of comparing predetermined characteristics of a known population of examination subjects to the corresponding values resulting from said cumulation of weighted values, and assigning correlated qualitative examination subject characteristics to said cumulation values based on such comparison.

25. The method as set forth in claim 24, wherein said step of assigning qualitative examination subject characteristics to said cumulation values comprises percentile categorization of the presence of such characteristics.

* * * * *